United States Patent [19]
De Salvert et al.

[11] Patent Number: 5,788,972
[45] Date of Patent: Aug. 4, 1998

[54] PRODUCT FOR TOPICAL APPLICATION CONTAINING A LIPASE AND AN ACTIVE INGREDIENT PRECURSOR

[75] Inventors: Armelle De Salvert, Paris; Daniel Sera, L'Hay-les-Roses; Gerard Guth, Montmorency; Pierre Fodor, Garches; Emmanuelle Maurin, L'Isle-Adam, all of France

[73] Assignee: L'Oreal, Paris, France

[21] Appl. No.: 547,146

[22] Filed: Oct. 24, 1995

[30] Foreign Application Priority Data

Oct. 24, 1994 [FR] France .................. 94 12684

[51] Int. Cl.$^6$ .................................................... A61K 7/48
[52] U.S. Cl. .................. 424/401; 424/59; 424/62; 514/474; 514/549; 514/552; 514/844; 514/846; 514/847; 514/937
[58] Field of Search ................... 424/59, 62, 401; 514/844, 846, 847, 549, 552, 937

[56] References Cited

U.S. PATENT DOCUMENTS 4,556,554  12/1985  Calvo .......................... 424/70
5,124,313   6/1992  Schaffer et al. ................. 514/2

FOREIGN PATENT DOCUMENTS

A-2 211 209  7/1974  France .
A-2 556 218  6/1985  France .
83 03061     9/1983  WIPO .

OTHER PUBLICATIONS

Shimizu, *Patent Abstracts of Japan*, vol. 12, No. 333 (C-526) [3180], corresponding to JP-A-63 096109.
Mori et al, *Patent Abstracts of Japan*, vol. 14, No. 294 (C-732) [4237], corresponding to JP-A-02 096510.

*Primary Examiner*—Jyothsan Venkat
*Attorney, Agent, or Firm*—Oblon, Spivak, McClelland, Maier & Neustadt, P.C.

[57] ABSTRACT

The present invention concerns a product for topical application, capable of releasing a cosmetic and/or dermatological active ingredient in and/or on the skin, containing a lipase enzyme and at least one ester precursor of the active ingredient. The ester contains an ester functional group having a saturated or unsaturated, linear or branched chain having from 2 to 25 carbon atoms. According to a preferred embodiment, the precursor and lipase are packaged so as not to be in contact with one another until the time of application to the skin.

20 Claims, No Drawings

PRODUCT FOR TOPICAL APPLICATION CONTAINING A LIPASE AND AN ACTIVE INGREDIENT PRECURSOR

BACKGROUND OF THE INVENTION

1. Field of the Invention

The present invention concerns a product for topical application which is capable of releasing a cosmetic and/or dermatological active ingredient on the skin and its use in the cosmetic and/or dermatological treatment of the skin, including the scalp.

2. Discussion of the Background

It is known to introduce active ingredients into cosmetic and/or dermatological compositions for the purpose of contributing specific treatments to the skin, for example in combating drying, aging or pigmentation of the skin, for treating acne or certain skin diseases (eczema, psoriasis), for combating excess weight, for promoting restructuring of the skin or its cell renewal, and for dyeing the skin.

For example, ascorbic acid (or vitamin C) is known for stimulating the growth of connective tissue, especially collagen. It also makes it possible to reinforce the defenses of cutaneous tissue against external attacks, such as ultraviolet radiation or pollution. It is also used for removing stains and pigmentation from the skin, and also for promoting healing of the skin.

Application of retinol or vitamin A makes it possible to combat in particular cutaneous aging and to combat certain skin disorders, such as acne or disorders of keratinization or of healing.

In addition, tocopherols, such as vitamin E, are known to have antioxidizing properties with respect to phospholipids of the cell membrane and properties in counteracting free radicals (see "Radicaux libres et Vitamine E [Free radicals and vitamin E]" by J. B. Chazan and M. Szulc - Cah. Nutr. Diet., 1987, 6, XXII, 1, pages 66 to 76).

Moreover, application of dihydroxyacetone to the skin makes it possible to provide the appearance of a suntan on the skin, without the disadvantages (burns, cancer risk) encountered during exposure to the sun.

Unfortunately, certain active ingredients, and in particular those mentioned above, are unstable and are sensitive to external factors such as light or heat. This instability goes against the desired effectiveness and can, moreover, be a source of annoyance to the user, for example when the instability of the active ingredient leads to modifications in the color and/or smell of the composition containing it.

Consequently, various means have been envisaged for stabilizing these active ingredients. For example, one such means involves blocking the reactive site of the active ingredient by esterification, in particular with phosphate, sulphate or alkyl derivatives, and in using the derivatives in place of the free active ingredient. Unfortunately, the derivatives are not as effective as the free active ingredient.

It has also been envisaged to use precursors of such active ingredients, which, after application to the skin, are converted by cutaneous enzymes to the free active ingredient. For example, European patent publication No. EP-A-487,404 discloses the use of a glucosylated derivative of ascorbic acid in dermatological compositions which is easily hydrolysed by cutaneous enzymes and thus capable of releasing ascorbic acid when these compositions are applied to the skin. However, the use of such derivatives does not make possible rapid release, in a sufficient amount, of ascorbic acid at the surface of the skin.

Thus, there remains the need for products for topical application containing cosmetic and/or dermatological active ingredients in which the active ingredients retain their properties and effectiveness with time.

SUMMARY OF THE INVENTION

Accordingly, one object of the present invention is to provide novel compositions for topical application to the skin which stabilize the effective ingredient(s) but which minimize or eliminate any reduction of the effectiveness of the active ingredient(s).

A further object of the present invention is to provide novel methods of protecting the skin or of delivering a cosmetically and/or dermatologically active ingredient to the skin, using a composition in which the effective ingredient(s) are stabilized but in which the effectiveness of the active ingredient(s) is not significantly reduced.

These and other objects of the present invention, which will be readily understood in the context of the following detailed description of the preferred embodiments, have been provided by a product for topical application, comprising a lipase and at least one precursor of a cosmetic and/or dermatological active ingredient, wherein the precursor is an ester containing at least one ester functional group having a saturated or unsaturated, linear or branched carbon chain of from 2 to 25 carbon atoms.

DESCRIPTION OF THE PREFERRED EMBODIMENTS

The present Inventors have unexpectedly found that compositions containing an enzyme, lipase, in combination with esters of unstable active ingredients, and use of the same to protect or deliver active ingredients to the skin avoid the disadvantages of prior approaches.

Consequently, the present invention concerns a product for topical application containing a lipase and at least one precursor of a cosmetic and/or dermatological active ingredient, wherein the precursor is an ester containing at least one ester functional group having a saturated or unsaturated, linear or branched chain having from 2 to 25 carbon atoms.

In the context of the present application, "product" is understood to mean both cosmetic and dermatological compositions, as well as commercial devices further comprising a container in which the enzyme and precursor components of the present composition are housed in isolation from one another.

Lipase is an enzyme known to hydrolyze triglycerides to diglycerides, monoglycerides, glycerol and/or free fatty acids. It is used in particular in detergents (see the article "Lipases as detergent components", H. Andree et al., Journal of Applied Biochemistry, 1980, vol. 2, pages 218 to 229) to remove greasy stains such as those arising from frying fats, oils, sebum or greasy cosmetics such as lipsticks. Due to its ability to hydrolyze triglycerides, it has been used in the cosmetics field in an immobilized form for cleaning the skin (see, for example, U.S. Pat. No. 4,556,554).

The lipase used in the present invention should be sufficiently stable to retain its enzymatic activity. The present lipase preferably belongs to the group of enzymes of EC 3.1.1.3. classification, which corresponds to a lipase which hydrolyses the ester bonds at the 1- and 3- positions of a triglyceride. It can be chosen, for example, from those lipases sold under the tradenames "LIPASE SP644" and "LIPOLASE 100 L" by the company Novo Nordisk.

The lipase used in the present product may be included in an amount ranging from 0.05% to 30% by weight, preferably from 0.1 to 10% by weight, and more preferably from 0.1 to 5% by weight with respect to the total weight of the composition (e.g., the combination of lipase, ester, cosmetically and/or dermatologically acceptable medium or carrier, additives, adjuvants, etc., not including the weight of any container or packaging in which the composition is contained).

The active ingredients which may be suitable for use in the present invention include those containing at least one hydroxyl or carboxyl functional group, preferably hydroxyl group, and in particular, esterifiable vitamins, such as retinol (vitamin A) and its derivatives, ascorbic acid (vitamin C) and its derivatives, and hydroxylated ketones, such as dihydroxyacetone.

The active ingredient precursor used according to the present invention is an ester containing one or more ester functional groups having a saturated or unsaturated, linear or branched chain having from 2 to 25 carbon atoms and optionally containing one or more substituents. The ester functional group is preferably one of the formula —O—C(=O)—R (i.e., an ester of an active ingredient containing a hydroxyl functional group) or a group of the formula —C(=O)—O—R (i.e., an ester of an active ingredient having a carboxyl functional group), in which R is an alkyl group having from 1 to 24 carbon atoms or an alkenyl or alkynyl group having from 2 to 24 carbon atoms which may contain one or more sites of ethylenic unsaturation.

The carbon chain of the ester functional group is chosen in particular from acyl, benzoyl, alkylbenzoyl, acylbenzoyl and 2-hydroxyphenylacetyl radicals, which are optionally substituted. Preferably, "acyl" refers to a group of the formula —C(=O)—R, where R is as described above.

The substituent can be hydroxyl, halogen, alkoxy of from 1 to 4 carbon atoms or phenyl, and is preferably a hydroxyl radical.

In a preferred embodiment of the present invention, the carbon chain of the ester functional group has from 12 to 18 carbon atoms.

The present ester may be chosen from $C_1$–$C_{24}$ alkanoic, alkenoic, alkynoic, cycloalkanoic, aryl (e.g., phenyl, naphthyl) and aralkyl carboxylic acids (which may be substituted as described above), and particularly, from esters of lauric acid, palmitic acid, stearic acid, cetylic acid, myristic acid, linoleic acid, octanoic acid, oleic acid, butyric acid, propionic acid, acetic acid, salicylic acid, lactic acid, cinnamic acid, or derivatives thereof, such as ferulic acid, or mixtures thereof.

The ester used in the present invention can be, for example, dihydroxyacetone monolaurate, dihydroxyacetone dilaurate, dihydroxyacetone monostearate, dihydroxyacetone distearate, dihydroxyacetone monopalmitate, dihydroxyacetone dipalmitate, ascorbyl palmitate, ascorbyl laurate, ascorbyl myristate, ascorbyl stearate, ascorbyl nicotinate, retinyl palmitate, retinyl propionate, retinyl acetate, retinyl butyrate, retinyl octanoate, retinyl laurate, retinyl oleate, retinyl linoleate and/or a mono- and/or diester of cinnamic acid or a derivative thereof, such as esters described, for example, in FR-A-2715156, and in particular, 2-O-ascorbyl ferulate and 2-O-(6-palmitoylascorbyl)-4'-acetoxy ferulate.

When the precursor is a vitamin ester, the ester may be present in an amount of from 0.1 to 50% by weight, and preferably from 0.5 to 10% by weight, with respect to the total weight of the composition. When the precursor is an ester of a ketone, and in particular, an ester of dihydroxyacetone, the ester may be present in an amount of from 5 to 30% by weight with respect to the total weight of the composition.

According to a first variant of the present invention, the lipase and the precursor are present in a single composition which preferably is prepared just before use.

According to a second variant, the lipase and the precursor are packaged so as not to be in contact with one another, for example, in two different compositions, each contained in a separate compartment in a product. The separate compositions can either be (a) mixed at the time of application, (b) applied to the skin successively, or (c) successively applied to the skin with a time delay (e.g., one composition can be applied to the skin, then after waiting for a period of time of from, e.g., 30 seconds to 1 hour, the second composition may be applied to the same location).

It is also possible, for example, to arrange the compositions in a product comprising two compartments which communicate with a shared pipe or tube from which they can exit while simultaneously being mixed. The combined compositions thus mixed may then be applied to the skin. Such two-compartment packaging devices are, for example, described in FR-A-2,045,559, FR-A-2,105,332, FR-A-2,258,319, FR-A-2,293,375, FR-A-2,586,913, FR-A-2,643,615, U.S. Pat. No. 3,964,643 and U.S. Pat. No. 4,823,985.

It is also possible to produce one of the compositions in an encapsulated form and/or in the form of microcapsules or of microgranules immersed in the other composition, the microcapsules or the microgranules being crushed at the time of application by rubbing against the skin, which thus makes possible mixing of the lipase and of the precursor and release of the free active ingredient on the skin.

The present product advantageously contains an inert medium or carrier appropriate for topical application, particularly a cosmetically and/or dermatologically acceptable medium or carrier. The cosmetically and/or dermatologically acceptable medium generally comprises water, a mixture of water and fatty substance or a mixture of fatty substances.

Fatty substances which can be used in the present invention include mineral oils (petrolatum, mineral oil), vegetable oils and their hydrogenated derivatives, animal oils, synthetic oils, silicone oils (dimethicone, cyclomethicone), fluorinated oils and other fatty substances, such as fatty alcohols, fatty acids and waxes.

In particular, the present product can be provided in the form of aqueous, alcoholic or aqueous/alcoholic solutions, hydrophilic or lipophilic gels, microemulsions and water-in-oil, oil-in-water, water-in-oil-in-water or oil-in-water-in-oil emulsions having the appearance of a cream or gel, which are optionally capable of foaming. The present product can also be provided in the form of an aerosol, or alternatively, in the form of vesicular dispersions containing ionic and/or nonionic lipids. These pharmaceutical dosage forms are prepared according to known methods in the cosmetic and dermatological fields.

In accordance with known methods and compositions in the cosmetic and dermatological fields, the medium appropriate for topical application in accordance with the present invention can also contain conventional adjuvants, such as hydrophilic or lipophilic gelling agents, surfactants, hydrophilic or lipophilic active agents, preservatives, antioxidants, solvents, fragrances, fillers, screening agents and coloring materials.

The amounts of the various constituents of the present product may be those amounts conventionally used in the cosmetics and dermatological fields.

An additional subject of the present invention is the use of the present product for preparing a dermatological salve or ointment for protection and/or therapeutic treatment of the skin.

The present product can be used, depending on the active ingredient ester which it contains, for the cosmetic and/or dermatological treatment of the skin. Thus, the present invention concerns a method of protecting the skin and/or of delivering an active ingredient to the skin, comprising applying the present composition to skin in need thereof.

The present invention also concerns a process for cosmetically treating skin, comprising applying to the skin, simultaneously or with a time delay, a lipase and at least one precursor of a cosmetically or dermatologically active ingredient, wherein the precursor is an ester containing at least one ester functional group having a saturated or unsaturated, linear or branched chain having from 2 to 25 carbon atoms.

The present product can in particular constitute protection, treatment or care products for the face, for the neck, for the hands or for the body, artificial tanning products or products for the hair, and in particular for caring for the scalp, for example in the form of shampoos, of treatment lotions, of styling creams or gels, or of lotions and/or gels for combating hair loss.

Other features of the present invention will become apparent in the course of the following descriptions of exemplary embodiments which are given for illustration of the invention, and are not intended to be limiting thereof. The examples which follow are given by way of illustration in order to make the invention better understood. The amounts indicated are percentages by weight.

EXAMPLES

EXAMPLE 1

Care Cream for Depigmenting the Skin

| Oily phase: | |
|---|---|
| Triceteareth-4 phosphate/sodium $C_{14}$–$C_{17}$ alkyl sec sulphonate (HOSTACERIN CG, sold by Hoechst Celanese) (surfactant) | 6% |
| Petrolatum | 2% |
| Mineral oil | 4% |
| Dimethicone | 3% |
| Cyclomethicone | 3% |
| Dimethicone copolyol (surfactant) | 1% |
| Triclosan (preservative) | 0.1% |
| Ascorbyl palmitate | 1% |
| Aqueous phase | |
| Propylene glycol (humectant) | 2% |
| PEG-20 (organoleptic) | 1% |
| LIPOLASE 100 L | 1% |
| Phenoxyethanol (preservative) | 0.4% |
| Water | q.s. for 100% |

The LIPOLASE 100 L is introduced into the aqueous phase in the encapsulated form (in microcapsules also containing atelocollagen and glycosaminoglycans). The microcapsules are mixed with the remainder of the constituents after preparation of the emulsion.

EXAMPLE 2

Anti-wrinkle Cream

| Oily phase: | |
|---|---|
| Triceteareth-4 phosphate/sodium $C_{14}$–$C_{17}$ alkyl sec sulphonate (HOSTACERIN CG, sold by Hoechst Celanese) (surfactant) | 6% |
| Petrolatum | 2% |
| Mineral oil | 4% |
| Dimethicone | 3% |
| Cyclomethicone | 3% |
| Dimethicone copolyol (surfactant) | 1% |
| Triclosan (preservative) | 0.1% |
| Retinyl palmitate | 1% |
| Aqueous phase | |
| Propylene glycol (humectant) | 2% |
| PEG-20 (organoleptic) | 1% |
| LIPOLASE 100 L | 1% |
| Phenoxyethanol (preservative) | 0.4% |
| Water | q.s. for 100% |

The retinyl palmitate is introduced into the composition in the form of microspheres also containing atelocollagen and glycosaminoglycans. The microspheres are mixed with the remainder of the constituents after preparation of the emulsion.

EXAMPLE 3

Instant Tanning Suncream

| A. Emulsion containing a dihydroxyacetone ester: | |
|---|---|
| Oily phase: | |
| Steareth-2 (surfactant) | 3% |
| Steareth-21 (surfactant) | 2% |
| PPG-15 stearyl ether (surfactant) | 29.5% |
| Dihydroxyacetone palmitate | 14.6% |
| Aqueous phase: | |
| Phenoxyethanol (preservative) | 0.5% |
| Water | q.s. for 100% |
| B. Emulsion containing the lipase: | |
| Oily phase: | |
| Steareth-2 (surfactant) | 3% |
| Steareth-21 (surfactant) | 2% |
| PPG-15 stearyl ether (surfactant) | 29.5% |
| Aqueous phase: | |
| Phenoxyethanol (preservative) | 0.5% |
| LIPASE SP644 | 2% |
| Water | q.s. for 100% |

The emulsions A and B are arranged in two separate compartments and are mixed at the time of application to the skin. The product obtained gives, after application to the skin, a progressively tanned coloring to the skin.

EXAMPLE 4

Instant Tanning Suncream

A. Emulsion containing a dihydroxyacetone ester:

Oily phase:

| | |
|---|---|
| Steareth-2 (surfactant) | 3% |
| Steareth-21 (surfactant) | 2% |
| PPG-15 stearyl ether (surfactant) | 29.5% |
| Dihydroxyacetone laurate | 10% |

Aqueous phase:

| | |
|---|---|
| Phenoxyethanol (preservative) | 0.5% |
| Water | q.s. for 100% |

B. Emulsion containing the lipase:

Oily phase:

| | |
|---|---|
| Steareth-2 (surfactant) | 3% |
| Steareth-21 (surfactant) | 2% |
| PPG-15 stearyl ether (surfactant) | 29.5% |

Aqueous phase:

| | |
|---|---|
| Phenoxyethanol (preservative) | 0.5% |
| LIPASE 100 L | 1% |
| Water | q.s. for 100% |

The emulsions are arranged in two different compartments and are brought into contact at the time of application.

EXAMPLE 5

Anti-wrinkle Cream

Oily phase:

| | |
|---|---|
| Triceteareth-4 phosphate/sodium $C_{14}$–$C_{17}$ alkyl sec sulphonate (HOSTACERIN CG, sold by Hoechst Celanese) (surfactant) | 5% |
| Stearyl alcohol | 1% |
| Petrolatum | 2% |
| Mineral oil | 4% |
| Phenyl trimethicone | 4% |
| Cyclomethicone | 4% |
| Dimethicone/Dimethiconol (surfactant) | 2% |
| Triclosan (preservative) | 0.1% |
| Retinyl palmitate | 0.6% |

Aqueous phase

| | |
|---|---|
| Propylene glycol (humectant) | 2% |
| PEG-20 (organoleptic) | 1% |
| LIPOLASE SP644 | 0.5% |
| Phenoxyethanol (preservative) | 0.2% |
| Chlorphenesin | 0.2% |
| Polyacrylamide/C13–C14 Isoparaffin/Laureth-7 (SEPIGEL 305, sold by Seppic) (gelling agent) | 0.6% |
| Water | q.s. for 100% |

The retinyl palmitate is introduced into the composition in the form of microspheres also containing atelocollagen and sodium chondroitin sulphate. The microspheres are mixed with the remainder of the constituents after preparation of the emulsion.

EXAMPLE 6

Care Cream for Depigmenting the Skin

A. Emulsion containing the ester of vitamin C:

Oily phase:

| | |
|---|---|
| Steareth-2 (surfactant) | 3% |
| Steareth-21 (surfactant) | 2% |
| PPG-15 stearyl ether (surfactant) | 9% |
| Cetyl alcohol | 2% |
| Petrolatum | 5% |
| Triclosan (preservative) | 0.2% |
| Ascorbyl palmitate | 1% |

Aqueous phase:

| | |
|---|---|
| Propylene glycol (humectant) | 4% |
| PEG-20 (organoleptic) | 5% |
| Phenoxyethanol (preservative) | 0.5% |
| Water | q.s. for 100% |

B. Emulsion containing the lipase:

Oily phase:

| | |
|---|---|
| Steareth-2 (surfactant) | 3% |
| Steareth-21 (surfactant) | 2% |
| PPG-15 stearyl ether (surfactant) | 9% |
| Cetyl alcohol | 2% |
| Petrolatum | 5% |
| Triclosan (preservative) | 0.2% |

Aqueous phase:

| | |
|---|---|
| Propylene glycol (humectant) | 4% |
| PEG-20 (organoleptic) | 5% |
| Phenoxyethanol (preservative) | 0.5% |
| LIPASE 100 L | 1% |
| Water | q.s. for 100% |

The emulsions A and B are arranged in two separate compartments and are brought into contact at the time of application to the skin.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letter Patent of the United States is:

1. A product for topical application, comprising a lipase and at least one precursor of dihydroxyacetone, wherein said precursor is an ester containing at least one ester functional group having a saturated or unsaturated, linear or branched carbon chain of from 2 to 25 carbon atoms, which may be substituted.

2. The product of claim 1, wherein said ester functional group contains a radical selected from the group consisting of acyl, benzoyl, alkylbenzoyl, acylbenzoyl or 2-hydroxyphenylacetyl, each of which may be substituted.

3. The product of claim 1, wherein the chain of the ester functional group has from 12 to 18 carbon atoms.

4. The product of claim 1, wherein the ester is selected from the group consisting of esters of lauric acid, palmitic acid, stearic acid, cetylic acid, myristic acid, propionic acid, linoleic acid, acetic acid, butyric acid, octanoic acid, oleic acid, cinnamic acid, ferulic acid, and mixtures thereof.

5. The product of claim 1, wherein the lipase and the precursor are packaged so as not to be in contact with one another.

6. The product of claim 5, wherein the lipase and the precursor are packaged in separate compartments.

7. The product of claim 1, wherein the lipase, the precursor or both the lipase and the precursor are in an encapsulated form.

8. The product of claim 7, wherein the lipase, the precursor or both the lipase and the precursor are in the form of microcapsules or microgranules.

9. The product of claim 1, wherein the lipase is capable of hydrolyzing ester bonds at the 1- and 3-positions of a triglyceride.

10. The product of claim 1, wherein the lipase is present in an amount of from 0.05 to 30% by weight with respect to the total weight of the product not including the weight of any container or packaging.

11. The product of claim 10, wherein the lipase is present in an amount of from 0.1 to 10% by weight with respect to the total weight of the product not including the weight of any container or packaging.

12. The product of claim 1, wherein the precursor is present in an amount of from 0.1 to 50% by weight with respect to the total weight of the product not including the weight of any container or packaging.

13. A method of delivering a cosmetically and/or dermatologically active ingredient to the skin, comprising applying the product of claim 1 to skin in need thereof.

14. A process for cosmetically treating skin, comprising applying to the skin, simultaneously or after a time delay, a lipase and at least one precursor of dihydroxyacetone, wherein the precursor is an ester containing at least one ester functional group having a saturated or unsaturated, linear or branched chain having from 2 to 25 carbon atoms.

15. A method of preparing a dermatological salve or ointment for the therapeutic treatment of the skin, comprising mixing a lipase with a cosmetically and/or dermatologically acceptable medium in a container or vessel, and mixing in the same or a separate container or vessel, at least one precursor of dihydroxyacetone, wherein said precursor is an ester containing at least one ester functional group having a saturated or unsaturated, linear or branched chain of from 2 to 25 carbon atoms, which may be substituted.

16. The method of claim 13, wherein said application of said product causes coloring or artificial tanning of said skin.

17. A product for topical application, comprising a lipase and at least one precursor of a cosmetic and/or dermatological active ingredient, wherein said precursor is selected from the group consisting of dihydroxyacetone monolaurate, dihydroxyacetone dilaurate, dihydroxyacetone monostearate, dihydroxyacetone distearate, dihydroxyacetone monopalmitate, and dihydroxyacetone dipalmitate, and wherein said lipase is present in an amount from 0.05 to 30% by weight and said precursor is present in an amount of from 0.1 to 50% by weight, where said percent by weights are relative to the total weight of said product not including the weight of any container or packaging.

18. A method of delivering a cosmetically and/or dermatologically active ingredient to the skin, comprising applying the product of claim 17 to skin in need thereof.

19. A process for cosmetically treating skin, comprising applying to the skin, simultaneously or after a time delay, a lipase and at least one precursor of a cosmetic or dermatological active ingredient selected from the group consisting of dihydroxyacetone monolaurate, dihydroxyacetone dilaurate, dihydroxyacetone monostearate, dihydroxyacetone distearate, dihydroxyacetone monopalmitate, and dihydroxyacetone dipalmitate, wherein the weight ratio of lipase to precursor is 0.05–30/0.01–50.

20. A method of preparing a dermatological salve or ointment for the therapeutic treatment of the skin, comprising mixing a lipase with a cosmetically and/or dermatologically acceptable medium in a container or vessel, and mixing in the same or a separate container or vessel, at least one precursor of a cosmetic and/or dermatological active ingredient selected from the group consisting of dihydroxyacetone monolaurate, dihydroxyacetone dilaurate, dihydroxyacetone monostearate, dihydroxyacetone distearate, dihydroxyacetone monopalmitate, and dihydroxyacetone dipalmitate, wherein the weight ratio of lipase to precursor is 0.05–30/0.01–50.

* * * * *